United States Patent [19]

Glowka et al.

[11] Patent Number: 5,047,579

[45] Date of Patent: Sep. 10, 1991

[54] PROCESS FOR PRODUCING N-PHOSPHONOMETHYLGLYCINE

[75] Inventors: Jozef G. Glowka; Kai K. Lau, both of New South Wales, Australia; Henryk Krawczyk, Orzeszkowej, Poland; Donald L. Fields, Jr., Manchester, Mo.

[73] Assignee: Monsanto Company, St. Louis, Mo.

[21] Appl. No.: 543,002

[22] Filed: Jun. 25, 1990

[30] Foreign Application Priority Data

Jan. 26, 1990 [AU] Australia ............... PJ8339

[51] Int. Cl.$^5$ ............................... C07F 9/38
[52] U.S. Cl. ................................... 562/17
[58] Field of Search ......................... 562/17

[56] References Cited

U.S. PATENT DOCUMENTS

| | | | |
|---|---|---|---|
| 3,950,402 | 4/1976 | Franz | 260/502.5 |
| 3,954,848 | 5/1976 | Franz | 260/502.5 |
| 4,062,669 | 12/1977 | Franz | 562/17 |
| 4,579,689 | 4/1986 | Hershman et al. | 562/17 |
| 4,582,650 | 4/1986 | Felthouse | 562/17 |
| 4,853,159 | 8/1989 | Riley et al. | 562/17 |
| 4,898,972 | 2/1990 | Fields et al. | 562/17 |
| 4,952,723 | 8/1990 | Fields et al. | 562/17 |

FOREIGN PATENT DOCUMENTS 0187347 7/1981 Hungary.

Primary Examiner—J. E. Evans
Attorney, Agent, or Firm—Frank D. Shearin

[57] ABSTRACT

An improved process is disclosed for the preparation of N-phosphonomethylglycine by the oxidation of N-phosphonomethyliminodiacetic acid. In the process N-phosphonomethyliminodiacetic acid is oxidized with a peroxide to form an intermediate, N-phosphonomethyliminodiacetic acid-N-oxide, and thereafter, adding a metabisulfite compound in the presence of a molybdenum compound to convert the intermediate to N-phosphonomethylglycine.

16 Claims, No Drawings

PROCESS FOR PRODUCING N-PHOSPHONOMETHYLGLYCINE

BACKGROUND OF THE INVENTION

This invention relates to a process for the preparation of N-phosphonomethylglycine, and more particularly to the preparation of N-phosphonomethylglycine by the conversion of N-phosphonomethyliminodiacetic acid to N-phosphonomethylglycine using peroxides.

N-Phosphonomethylglycine, known also by its common name glyphosate, is a highly effective commercially important phytotoxicant useful in controlling a large variety of weeds. It is applied to the foliage of a very broad spectrum of annual and perennial grasses and broad leaf plants. Industrial uses include control of weeds along roadsides, waterways, transmission lines, in storage areas, and in other nonagricultural areas. Usually, N-phosphonomethylglycine is formulated into herbicidal compositions in the form of its various salts in solution, preferably water.

U.S. Pat. No. 3,950,402 to Franz discloses a process for the production of N-phosphonomethylglycine by forming an admixture of N-phosphonomethyliminodiacetic acid, water, and a metallic catalyst selected from the noble metals, heating the admixture to an elevated temperature (greater than 70° C. to avoid low yields) and contacting the admixture with a free oxygen-containing gas.

U.S. Pat. No. 3,954,848 to Franz discloses a process for the production of N-phosphonomethylglycine by reacting N-phosphonomethyliminodiacetic acid with an oxidizing agent, such as hydrogen peroxide, in an aqueous acidic medium in the presence of a strong acid at a temperature of from about 70° C. to about 100° C. It is disclosed that one should employ at least 2 moles of the hydrogen peroxide for each mole of the N-phosphonomethyliminodiacetic acid, and preferably more.

Hungarian Patent Application No. 187,347 discloses a process for the preparation of N-phosphonomethylglycine by the oxidation of N-phosphonomethyliminodiacetic acid with peroxides using a catalytic amount of a metal compound selected from compounds of silver, iron, tin, lead, manganese, or molybdenum. Molybdates are preferred. At temperatures lower than 80° C., usually a contaminated end-product is obtained. Typically, the reaction is carried out at a temperature of above 80° C. and preferably above 100° C. at pressures exceeding atmospheric.

Although satisfactory results are obtained by the above processes to make N-phosphonomethylglycine, all of them suffer from one or more disadvantages, such as the use of excessive amounts of peroxide, the use of strong mineral acids and/or reaction at elevated temperatures and pressures. Thus, there is a need for a process which provides N-phosphonomethylglycine in high yields at modest temperatures and at atmospheric pressure using substantially stoichiometric amounts of peroxide to oxidize the N-phosphonomethyliminodiacetic acid to the desired N-phosphonomethylglycine without using strong mineral acids such as hydrochloric acid or sulfuric acid.

SUMMARY OF THE INVENTION

This need is satisfied and other advantages are achieved in a process for producing N-phosphonomethylglycine by the oxidation of N-phosphonomethyliminodiacetic acid with a peroxide to form an intermediate N-phosphonomethyliminodiacetic acid-N-oxide, the improvement of which comprises
adding a catalytic amount of a metabisulfite compound in the presence of a catalytic amount of a water-soluble molybdenum compound to convert the intermediate to N-phosphonomethylglycine.

DETAILED DESCRIPTION OF THE INVENTION

According to the process of the present invention N-phosphonomethyliminodiacetic acid in an aqueous solution is contacted with a peroxide to form an intermediate compound, N-phosphonomethyliminodiacetic acid-N-oxide at a temperature below about 70° C. Thereafter, a catalytic amount of a metabisulfite compound in the presence of a catalytic amount of a water-soluble molybdenum compound (if not already present from the previous step) is added to the reaction mixture to convert the intermediate N-phosphonomethyliminodiacetic acid-N-oxide to N-phosphonomethylglycine.

A number of peroxides known to those skilled in the art can be used in the process of the present invention. Suitable peroxides include hydrogen peroxide, performic acid, peracetic acid, perbenzoic acid, peroxytrifluoracetic acid, benzoyl peroxide, benzene persulfonic acid, and the like. Hydrogen peroxide is preferred, and it is advantageous to use hydrogen peroxide in the form of a concentrated solution (say between about 30% and 60%).

The intermediate, N-phosphonomethyliminodiacetic acid-N-oxide, is known to those skilled in the art, and can be prepared by a number of methods. For example, the intermediate can be prepared by the teachings in U.S. Pat. No. 3,950,402 or U.S. Pat. No. 3,954,848, both to Franz. In Hungarian patent application 187,347 the intermediate is formed from N-phosphonomethyliminodiacetic acid using peroxides in the presence of compounds of silver, iron, tin, lead, manganese or molybdenum. In U.S. Pat. No. 4,062,669 to Franz an N-organo-N-phosphonomethylglycine is oxidized with peroxide under acidic or basic conditions. Other methods may be known to those skilled in the art.

In the process of the present invention it is preferred to contact N-phosphonomethyliminodiacetic acid with peroxides in the presence of a catalytic amount of a water soluble molybdenum compound, such as a molybdenum salt, at temperatures between about 20° C. and about 70° C. to form the intermediate N-phosphonomethyliminodiacetic acid-N-oxide.

The salts of molybdenum useful as catalysts to oxidize the N-phosphonomethyliminodiacetic acid into the N-phosphonomethyliminodiacetic acid-N-oxide, and also to convert the N-phosphonomethyliminodiacetic acid-N-oxide to N-phosphonomethylglycine are known to those skilled in the art. It is only necessary that the molybdenum salts are soluble in the reaction medium. Suitable molybdenum compounds include molybdenum halides such as molybdenyl trichloride and the like; alkali metal molybdates, such as sodium molybdate and the like; or more complex salts such as the ammonium or alkali metal dimolybdates. Sodium and ammonium molybdates are especially preferred.

The amount of catalyst to convert the N-phosphonomethyliminodiacetic acid to the intermediate N-phosphonomethyliminodiacetic acid-N-oxide can vary within wide limits. Concentrations between about 0.01 to about 5 wt. % catalyst, based on the weight of the N-phosphonomethyliminodiacetic acid, provide satisfactory results. At concentrations of less than about 0.01 wt. % catalyst, the reaction is slow, and at concentrations greater than 5 wt. %, no advantage can be seen, although such higher concentrations are not particularly harmful. It is preferred to use from about 0.01 to about 1.0 wt. % catalyst with respect to the amount of N-phosphonomethyliminodiacetic acid.

The temperature of the process in the present invention to convert the N-phosphonomethyliminodiacetic acid to the N-oxide intermediate can vary from as low as about 20° C. to about 70° C. Although temperatures below 20° C. can be used, such temperatures would require the use of cooling, and no advantage is to be obtained. At temperatures above about 70° C., degradation of the N-phosphonomethyliminodiacetic acid-N-oxide is observed which affects the final yield of the desired N-phosphonomethylglycine. Temperatures between about 20° C. and about 65° C. are preferred.

Regardless of the method by which the intermediate N-phosphonomethyliminodiacetic acid-N-oxide is prepared, the intermediate is contacted with a metabisulfite compound, such as an alkali metal metabisulfite, like sodium metabisulfite or potassium metabisulfite, or ammonium metabisulfite. Sodium metabisulfite is preferred. However, it has been found that if a catalytic amount of a water-soluble molybdenum compound is not present, poor yields of N-phosphonomethylglycine are obtained. Thus, if the reaction to convert the N-phosphonomethyliminodiacetic acid to the intermediate is catalyzed by a compound other than molybdenum, a small amount of a water-soluble molybdenum compound must be added along with the metabisulfite compound to insure high yields of the desired N-phosphonomethylglycine. In the preferred embodiment of this invention, a molybdenum compound, preferably sodium or ammonium molybdate is used to form the intermediate, and thereafter sodium metabisulfite is added to provide the desired N-phosphonomethylglycine.

The temperature required to convert the intermediate N-phosphonomethyliminodiacetic acid-N-oxide can vary within wide limits. It is preferred to add the metabisulfite compound at or near room temperature (about 20° C.) because gas evolution generally occurs, and thereafter heat the mixture to at least 50° C. Temperatures in excess of 100° C. can be used, but pressure may be required as will occur to those skilled in the art. Satisfactory results are obtained when the mixture is heated to between about 50° C. and 100° C.

In the process of the present invention, the amount of peroxide should be the stoichiometric amount required to convert the N-phosphonomethyliminodiacetic acid to the intermediate, N-phosphonomethyliminodiacetic acid-N-oxide. As will occur to those skilled in the art, when less than a stoichiometric amount of peroxide is used, the yield is lower. A slight excess of peroxide can be used, but higher quantities should be avoided because the excess peroxide reacts with the metabisulfite compound and can affect the conversion of the N-phosphonomethyliminodiacetic acid-N-oxide to the desired N-phosphonomethylglycine.

The amount of metabisulfite compound to convert the N-phosphonomethyliminodiacetic acid-N-oxide to the desired N-phosphonomethylglycine depends upon the amount of peroxide in excess of that required to produce the intermediate from the N-phosphonomethyliminodiacetic acid, since the peroxide will react with the metabisulfite compound. In addition to the amount of metabisulfite compound required to react with the excess peroxide, there should also be sufficient metabisulfite to catalyze the reaction of the N-phosphonomethyliminodiacetic acid-N-oxide to N-phosphonomethylglycine. The amount of metabisulfite compound remaining after reaction with the peroxide to act as a catalyst should be at least 0.01 wt. %, based on the amount of the N-phosphonomethyliminodiacetic acid-N-oxide. Excess metabisulfite compound as high as 1%, or even higher, can be used, but there does not seem to be an advantage to using higher concentrations for the conversion of the intermediate to N-phosphonomethylglycine. It is preferred to use between about 0.01 wt. % and about 1 wt. %, based on the weight of the N-phosphonoiminodiacetic acid-N-oxide.

In addition, a water soluble molybdate compound must also be present to obtain high conversions to the desired N-phosphonomethylglycine, and concentrations between about 0.01 wt. % and about 5 wt. %, based on the weight of the N-phosphonomethyliminodiacetic acid-N-oxide, are preferred. If a water-soluble molybdate compound is used as the catalyst to convert the N-phosphonomethyliminodiacetic acid to the intermediate and is not removed from the reaction medium, a sufficient amount of the molybdate compound will be present in the reaction mixture when the metabisulfite compound is added, and this is what we prefer to do.

The concentration of the N-phosphonomethyliminodiacetic acid as the starting material can vary within wide limits in the preferred process of the present invention. For example, an aqueous suspension containing up to 50 wt. % N-phosphonomethyliminodiacetic acid can be used. Higher concentrations of the N-phosphonomethyliminodiacetic acid can be used, but it can present processing difficulties because of the thickness of the slurry. On the other hand, an aqueous solution of the N-phosphonomethyliminodiacetic acid containing about 5 wt. % of the N-phosphonomethyliminodiacetic acid can also be used. Lower concentrations can also be used, but it requires processing large volumes of liquid in the process of the present invention. It is preferred to use an aqueous slurry containing from about 20 wt. % to about 40 wt. % of the N-phosphonomethyliminodiacetic acid.

The N-phosphonomethyliminodiacetic acid starting material can be prepared by methods known to those skilled in the art. For example, this material can be produced by the reaction of formaldehyde, iminodiacetic acid and orthophosphorous acid in the presence of sulfuric acid. Although the N-phosphonomethyliminodiacetic acid mixture resulting from this reaction can be employed directly in the process of this invention, it is preferred to isolate the N-phosphonomethyliminodiacetic acid and then employ it in the process of this invention.

This invention is further illustrated by, but not limited to, the following examples. Conversion is calculated by dividing the moles of other compounds produced by the moles of starting N-phosphonomethyliminodiacetic acid, and multiplying by 100. Selectivity is calculated by dividing the moles of N-phosphonomethylglycine produced by the moles of N-phosphonomethyliminodiacetic acid converted and multiplying by 100.

EXAMPLE 1

This example illustrates the process of this invention using a slurry containing 27.5% N-phosphonomthyliminodiacetic acid.

To a 100 ml round-bottomed glass flask was added water (37 ml), N-phosphonomethyliminodiacetic acid (14.0 g), 30% hydrogen peroxide (7.2 g), and ammonium dimolybdate tetrahydrate (0.32 g). The mixture was heated to 65° C. and maintained at this temperature until a solution was obtained (about 30 minutes) indicating the N-oxide was found. The solution was then allowed to cool to 45° C. and stirred for 50 minutes. After cooling to room temperature sodium metabisulfite (0.25 g) in water (5 ml) was added to the solution. Gas evolution was observed, and the temperatuure of the solution rose to 65° C. The reaction mixture was allowed to cool to room temperature, the solids were filtered, and the filtrate and solids were analyzed by HPLC. The conversion of N-phosphonomethyliminodiacetic acid was 97.1% and the selectivity to N-phosphonomethylglycine was 93.3%.

EXAMPLE 2

This example illustrates the process of this invention when the concentration of the N-phosphonomethyliminodiacetic acid is increased to 50 wt. %.

To a 100 ml round-bottomed glass flask was added water (14 ml), N-phosphonomethyliminodiacetic acid (14.0 g), 30% hydrogen peroxide (7.2 g) and ammonium dimolybdate tetrahydrate (0.32 g). The mixture was heated to 65° C. and maintained at this temperature until a solution was obtained (about 50 minutes), indicating the N-oxide was formed. The solution was allowed to cool to 45° C., and it was stirred for 50 minutes. After cooling to room temperature, sodium metabisulfite (0.25 g) in water (5 ml) was added to the solution. Gas evolution was observed, and the temperature of the solution rose to 65° C. The reaction mixture was allowed to cool to room temperature, the solids were filtered, and the solids and filtrate were analyzed by HPLC. The conversion of N-phosphonomethyliminodiacetic acid was 93.0% and the selectivity to N-phosphonomethylglycine was 91.8%.

EXAMPLE 3

This example illustrates the effect of the metabisulfite in the process of the present invention.

A. To a 100 ml round-bottomed flask was added water (37.2 ml) and ammonium dimolybdate tetrahydrate (0.08 g). The mixture was stirred until a solution was obtained (about 20 seconds). Then, N-phosphonomethyliminodiacetic acid (3.5 g) was added along with 30% hydrogen peroxide (1.6 g). The mixture was heated with stirring to 45° C. until solution was obtained (about 50 minutes). No sodium metabisulfite was added. The solution was heated to reflux overnight. Analysis by HPLC showed that the conversion of N-phosphonomethyliminodiacetic acid was 81.3% and the selectivity to N-phosphonomethylglycine was 74.6%.

B. The procedure of part A was repeated except that after solution was obtained, the solution was heated at 45° C. for an additional 1.5 hours. Then, the solution was allowed to cool to 40° C. and sodium metabisulfite (2.0 g) in water (3.5 ml) was added over a 15 second period. The temperature increased to 50° C. The solution was heated to reflux overnight. Analysis by HPLC showed that the conversion of N-phosphonomethyliminodiacetic acid was 94.1% and the selectivity to N-phosphonomethylglycine was 94.5%.

EXAMPLE 4

This example illustrates the effect of the presence of a molybdenum compound to convert the intermediate N-phosphonomethyliminodiacetic acid-N-oxide to N-phosphonomethylglycine with metabisulfite.

The procedure of Example 3B was repeated except that sodium tungstate dihydrate (0.16 g) was used instead of the ammonium dimolybdate as a catalyst to convert N-phonosphonomethyliminodiacetic acid to N-phosphonomethyliminodiacetic acid-N-oxide. The bisulfite decomposition of the N-phosphonomethyliminodiacetic acid-N-oxide, as determined by HPLC analysis, showed that the selectivity to N-phosphonomethylglycine was only 78.4% and that the conversion of N-phosphonomethyliminodiacetic acid was only 33.6%.

Although the invention has been described in terms of specified embodiments which are set forth in considerable detail, it should be understood that this by way of illustration only, and that alternative embodiments and operating techniques will become apparent to those skilled in the art in view of the disclosure. Accordingly, modifications can be made without departing from the spirit of the described invention.

What is claimed is:

1. In a process for producing N-phosphonomethylglycine by the oxidation of N-phosphonomethyliminodiacetic acid with a peroxide to form an intermediate N-phosphonomethyliminodiacetic acid-N-oxide, the improvement which comprises:
    adding a catalytic amount of a metabisulfite compound in the presence of a catalytic amount of water-soluble molybdenum compound to convert the intermediate to N-phosphonomethylglycine.

2. In the process of claim 1 wherein the N-phosphonomethyliminodiacetic acid is oxidized in the presence of a water-soluble molybdate compound as the catalyst.

3. In the process of claim 2 wherein the molybdate compound is ammonium molybdate.

4. In the process of claim 2 wherein the molybdate compound is sodium molybdate.

5. In the process of claim 1 wherein the temperatures to form the intermediate is maintained between about 20° C. and 65° C.

6. In the process of claim 1 wherein the metabisulfite compound is an alkali metal metabisulfite.

7. In the process of claim 6 wherein the alkali metal metabisulfite is sodium metabisulfite.

8. In the process of claim 2 wherein the amount of catalyst to form the intermediate is between about 0.01 and about 5 wt. %, based on the weight of the N-phosphonomethyliminodiacetic acid.

9. In the process of claim 8 wherein the amount of catalyst is between about 0.01 and about 1.0 wt. %.

10. In the process of claim 1 wherein the amount of metabisulfite compound over that required to react with excess peroxide is at least 0.01 wt. %, based on the weight of the intermediate present.

11. In the process of claim 10 wherein the amount of metabisulfite compound is between 0.01 and about 1.0 wt. %.

12. In the process of claim 1 wherein the amount of molybdenum compound present along with the metabisulfite compound is between about 0.01 wt. % and about 1.0 wt. % based on the weight of the N-phosphonomethyliminodiacetic acid-N-oxide.

13. In the process of claim 1 wherein the peroxide is hydrogen peroxide.

14. In the process of claim 1 wherein the N-phosphonomethyliminodiacetic acid is contacted with hydrogen peroxide in the presence of ammonium molybdate catalyst at a temperature between about 20° C. and about 70° C. to form an intermediate, and thereafter, adding a catalytic amount of sodium metabisulfite to convert the intermediate to N-phosphonomethylglycine.

15. In the process of claim 14 wherein the amount of ammonium molybdate is between about 0.01 wt. % and about 5 wt. %, based on the amount of N-phosphonomethyliminodiacetic acid.

16. In the process of claim 15 wherein the amount of sodium metabisulfite over that required to react with excess hydrogen peroxide is between about 0.01 wt. % and about 1.0 wt. % based on the weight of N-phosphonomethyliminodiacetic acid-N-oxide present.

* * * * *